US011517616B2

(12) United States Patent
Ueno et al.

(10) Patent No.: US 11,517,616 B2
(45) Date of Patent: Dec. 6, 2022

(54) COMPOSITE POLYPEPTIDE MONOMER, AGGREGATE OF SAID COMPOSITE POLYPEPTIDE MONOMER HAVING CELL PENETRATION FUNCTION, AND NOROVIRUS COMPONENT VACCINE FOR SUBCUTANEOUS, INTRADERMAL, PERCUTANEOUS, OR INTRAMUSCULAR ADMINISTRATION AND HAVING SAID AGGREGATE AS EFFECTIVE COMPONENT THEREOF

(71) Applicants: DENKA COMPANY LIMITED, Tokyo (JP); TOKYO INSTITUTE OF TECHNOLOGY, Tokyo (JP); THE KITASATO INSTITUTE, Tokyo (JP); JAPAN AS REPRESENTED BY DIRECTOR-GENERAL OF NATIONAL INSTITUTE OF INFECTIOUS DISEASES, Tokyo (JP)

(72) Inventors: Takafumi Ueno, Tokyo (JP); Kengo Yoshikawa, Tokyo (JP); Megumi Mano, Tokyo (JP); Kazuhiko Katayama, Tokyo (JP); Motohiro Miki, Tokyo (JP); Reiko Todaka, Tokyo (JP); Yoshimasa Takahashi, Tokyo (JP); Taishi Onodera, Tokyo (JP)

(73) Assignees: Denka Company Limited, Tokyo (JP); TOKYO INSTITUTE OF TECHNOLOGY, Tokyo (JP); THE KITASATO INSTITUTE, Tokyo (JP); DIRECTOR-GENERAL OF NATIONAL INSTITUTE OF INFECTIOUS DISEASES, Tokyo (JP)

( * ) Notice: Subject to any disclaimer, the term of this patent is extended or adjusted under 35 U.S.C. 154(b) by 692 days.

(21) Appl. No.: 16/343,903

(22) PCT Filed: Oct. 19, 2017

(86) PCT No.: PCT/JP2017/037899

§ 371 (c)(1),
(2) Date: Apr. 22, 2019

(87) PCT Pub. No.: WO2018/074558

PCT Pub. Date: Apr. 26, 2018

(65) Prior Publication Data

US 2021/0299240 A1 Sep. 30, 2021

(30) Foreign Application Priority Data

Oct. 23, 2016 (JP) ............................ JP2016-207417

(51) Int. Cl.

| | |
|---|---|
| ***A61K 39/125*** | (2006.01) |
| ***C07K 14/085*** | (2006.01) |
| ***C12P 21/02*** | (2006.01) |

(52) U.S. Cl.

CPC .......... *A61K 39/125* (2013.01); *C07K 14/085* (2013.01); *C12P 21/02* (2013.01)

(58) Field of Classification Search

None

See application file for complete search history.

(56) References Cited

U.S. PATENT DOCUMENTS

| | | | |
|---|---|---|---|
| 2007/0166769 | A1 | 7/2007 | Lorens et al. |
| 2007/0207526 | A1 | 9/2007 | Coit et al. |
| 2010/0215649 | A1 | 8/2010 | Frye et al. |

FOREIGN PATENT DOCUMENTS

| | | | |
|---|---|---|---|
| EP | 1849798 | A1 | 10/2007 |
| JP | 2006-219435 | A | 8/2006 |
| JP | 2010-516758 | A | 5/2010 |
| JP | 2015-163056 | A | 9/2015 |
| WO | 2008/093982 | A1 | 8/2008 |
| WO | 2012140676 | A2 | 10/2012 |

(Continued)

OTHER PUBLICATIONS

PDB: 2Z6B_A. Chain A, Tail-associated lysozyme, dated Dec. 1, 2020.*

(Continued)

*Primary Examiner* — Nianxiang Zou

(74) *Attorney, Agent, or Firm* — Sughrue Mion, PLLC

(57) ABSTRACT

The present invention addresses the issue of providing a norovirus component vaccine for subcutaneous, intradermal, percutaneous, or intramuscular administration which vaccine can readily immunize the target cells, an associated product of a molecular needle serving as an active ingredient of the vaccine, and a production method for the associated product. The invention provides a norovirus component vaccine containing, as an active ingredient, an associated product including a hexamer formed through bonding of two molecules of a trimer of a molecular needle represented by the following formula (1). W-$L_1$-$X_n$—Y (1) [wherein W represents an amino acid sequence of P domain of the capsid protein of norovirus as an immunogen; $L_1$ represents a first linker sequence having 0 to 100 amino acids; X represents an amino acid sequence represented by SEQ ID NO: 1; Y represents an amino acid sequence of a cell introduction domain; n is an integer of 1 to 3].

8 Claims, 4 Drawing Sheets

Specification includes a Sequence Listing.

(56) References Cited

FOREIGN PATENT DOCUMENTS

WO 2012140676 A9 10/2012

OTHER PUBLICATIONS

NP_046771.1. baseplate assembly protein V [Bacteriophage P2]. Dated Oct. 11, 2021.*
WP_064580321.1. phage baseplate assembly protein V, partial [*Escherichia coli*], Apr. 17, 2020.*
YP_009012470.1. Phi92_gp138 [Enterobacteria phage phi92]. Dec. 20, 2020.*
International Search Report dated Jan. 23, 2018 in International Application No. PCT/JP2017/037899.
International Preliminary Report on Patentability dated Apr. 23, 2019 in International Application No. PCT/JP2017/037899.
Inaba et al., "Modulation of Cellular Functions by Protein Needles", Biophysics, vol. 55, No. 2, pp. 89-91, 2015 (8 pages total).
Maity et al., "Design of Bioinorganic Materials at the Interface of Coordination and Biosupramolecular Chemistry", The Chemical Record, vol. 17, No. 4, pp. 383-398, 2017 (16 pages total).
Communication dated Mar. 15, 2021 from the European Patent Office in Application No. 17 861 867.4.
Database Uniprot, https://www.uniprot.org/uniprot/Q7Y2C9.txt?version=53, retrieved from EBI accession No. UNIPROT:Q7Y2C9, Apr. 29, 2015, 2 pages total.
Y. Briers et al., "Stability analysis of the bacteriophage ϕKMV lysin gp36C and its putative role during infection", Cellular and Molecular Life Sciences, vol. 63, No. 16, Jul. 17, 2006, pp. 1899-1905 (7 pages total).
Anonymous: "Bacteriophages", retrieved from the Internet, https://www.ncbi.nlm.nih.gov/mesh/?term=Phage+%5BMeSH+Terms%5D", Jan. 1, 1975, 2 pages total.
Anonymous: "Viral Structural Proteins—MeSH-NCBI", retrieved from the internet, https://www.ncbi.nlm.nih.gov/mesh?Db=mesh&Cmd=DetailsSearch&Term=%22Viral+Structural+Proteins%22%5BMeSH+Terms%5D, Jan. 1, 1990, 2 pages total.
Communication dated Sep. 14, 2021 from the Japanese Patent Office in Application No. 2018-545748.
Vesikari et al., "Norovirus Vaccine: One Step Closer", Editorial Commentary, JID, vol. 211, Sep. 9, 2014, pp. 853-855.
Chroboczek et al., "Virus-like particles as vaccine", ACTA Biochimica Polonica, vol. 61, No. 3, Sep. 18, 2014, pp. 531-539.
Communication dated Apr. 23, 2020 by the European Patent Office in application No. 17861867.4.

* cited by examiner

[Fig. 1]
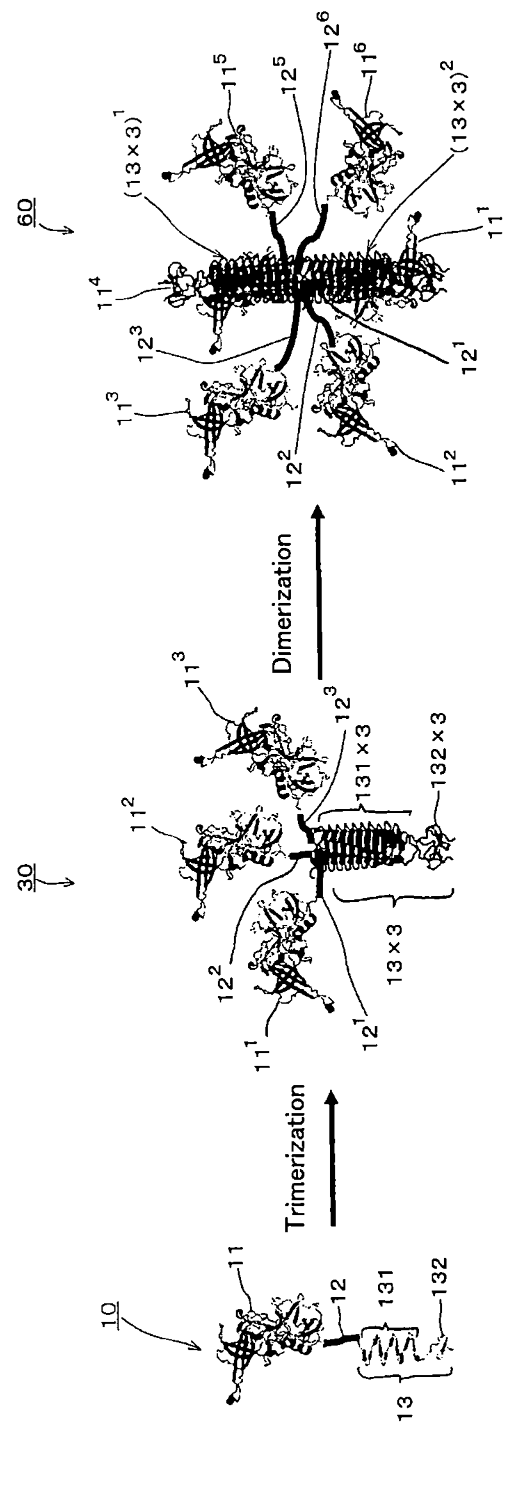

[Fig. 2]
SagaPF
Size exclusion column
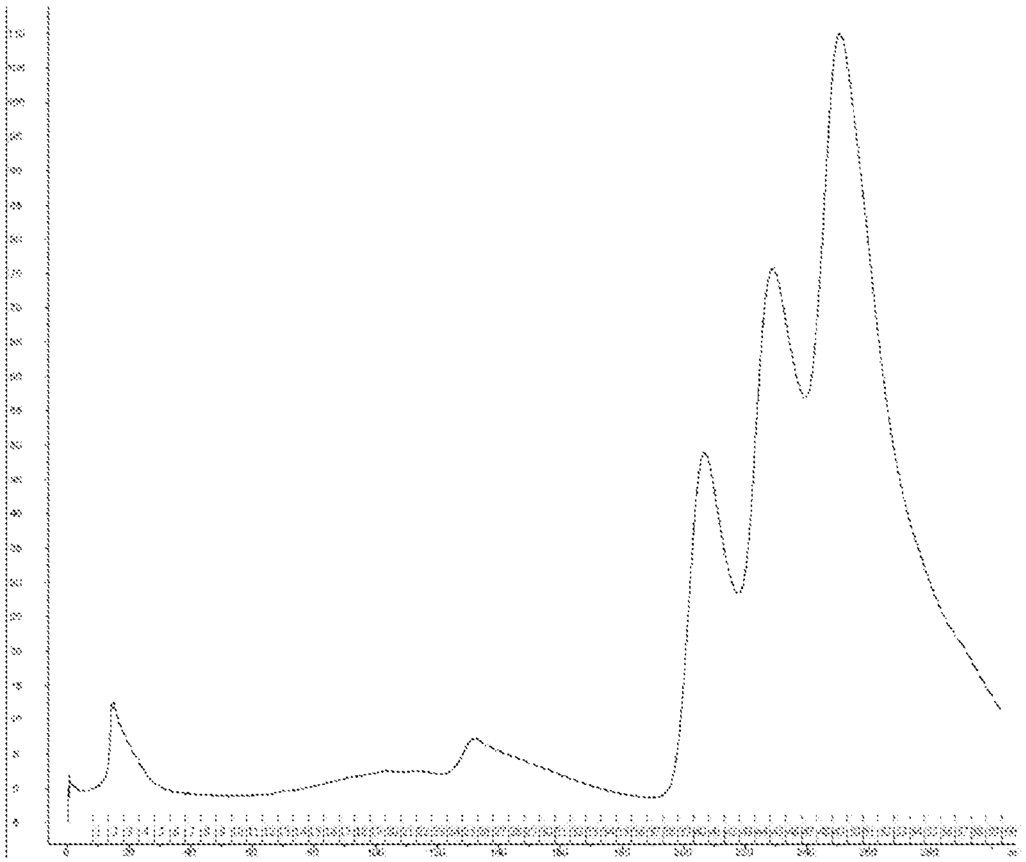

[Fig. 3]
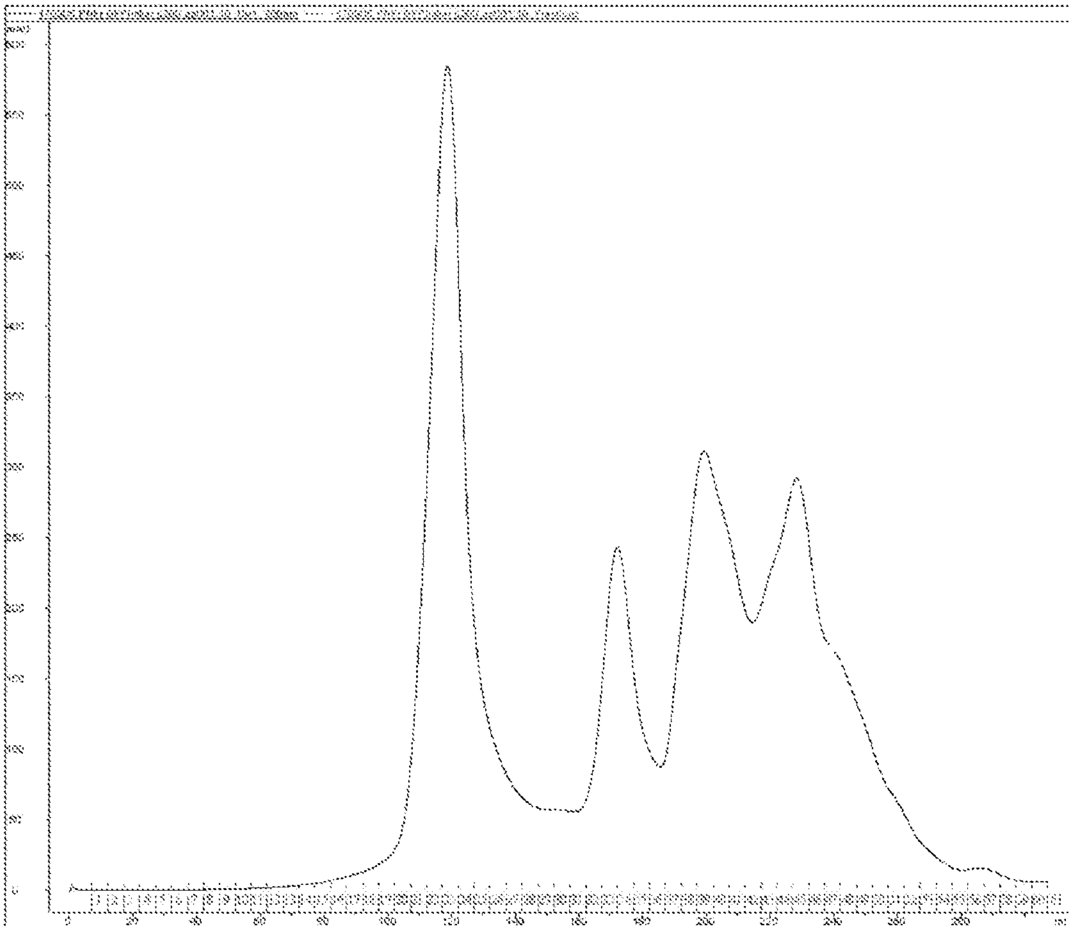

[Fig. 4]
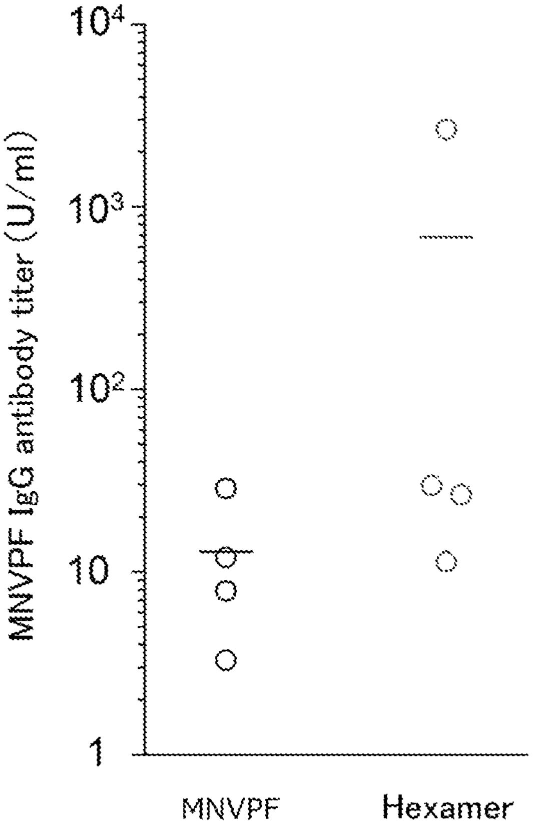

COMPOSITE POLYPEPTIDE MONOMER, AGGREGATE OF SAID COMPOSITE POLYPEPTIDE MONOMER HAVING CELL PENETRATION FUNCTION, AND NOROVIRUS COMPONENT VACCINE FOR SUBCUTANEOUS, INTRADERMAL, PERCUTANEOUS, OR INTRAMUSCULAR ADMINISTRATION AND HAVING SAID AGGREGATE AS EFFECTIVE COMPONENT THEREOF

CROSS REFERENCE TO RELATED APPLICATIONS

This application is a National Stage of International Application No. PCT/JP2017/037899 filed Oct. 19, 2017, claiming priority based on Japanese Patent Application No. 2016-207417, filed Oct. 23, 2016.

TECHNICAL FIELD

The present invention relates to a functional polypeptide and to a component vaccine containing the polypeptide for subcutaneous, intradermal, percutaneous, or intramuscular administration. More particularly, the invention relates to an associated product of a composite polypeptide monomer having a cell penetrating function which monomer is formed of an immunogen and a molecular needle, and to a norovirus component vaccine containing the associated product as an active ingredient (infection protective antigen (hereinafter simply referred to as protective antigen)), for subcutaneous, intradermal, percutaneous, or intramuscular administration.

BACKGROUND ART

Many vaccines for various infections have been provided, after smallpox vaccine had been developed by Edward Jenner and theoretical support for vaccine had been provided by Louis Pasteur.

Generally, vaccines are divided into three types: a live vaccine, a component vaccine, and a toxoid. The live vaccine employs a pathogenic microorganism (e.g., an attenuated virus) as a protective antigen. The component vaccine employs the entirety or a part of a killed pathogenic microorganism as a protective antigen. The toxoid employs a denatured toxin produced by a pathogen as a protective antigen.

Currently, vaccines are administered to subjects in need thereof mainly via subcutaneous injection or intramuscular injection.

Meanwhile, there has been provided a technique of "molecular needle," which has been developed by focusing on the excellent function of a bacteriophage to introduce genes into a cell.

PRIOR ART DOCUMENTS

Patent Documents

Patent Document 1: Japanese Patent Application Laid-Open (kokai) No. 2015-163056

DISCLOSURE OF THE INVENTION

Problems to be Solved by the Invention

Application of vaccines to various diseases is promising, but potential problems are involved in use of vaccines.

Vaccines are used to selectively induce immunoreaction by causing simulative infection of target tissue cells with a pathogenic microorganism by use of a protective antigen of interest. A vaccine is administered to blood via subcutaneous injection or intramuscular injection, while the vaccine is expected to be fed at random to target tissue cells by bodily functions. However, at present, it is difficult to efficiently introducing a protective antigen into the target tissue cells. As a result, the protective antigen must be used in an excessive amount greater than the amount of the antigen required for causing immunoreaction.

Means for Solving the Problems

In order to solve the aforementioned problem, the present inventors have focused on the "molecular needle" as mentioned above. The "molecular needle" has been developed mainly by one of the present inventors.

The inventors have assumed that a molecular needle to which a structural protein of a target virus as an immunogen has been attached, could be introduced into a target tissue cell at high efficiency due to an excellent function of the molecular needle to penetrate cells, via subcutaneous, intradermal, percutaneous, or intramuscular administration, to thereby cause an immunoreaction of interest, and the immunogen-attached molecular needle could be used as a protective antigen, and have accomplished the present invention.

As an example, when P domain of the capsid protein of a norovirus was used as an immunogen, a hexamer among the associated products falling within the scope of the present invention was found to exhibit excellent viral immunogenicity as a protective antigen. However, biological responses are diverse, and it is not clear at this time what kind of immune phenomenon the associated product of the present invention exhibits when using other immunogens.

The present invention provides the following four aspects:

(1) a "composite polypeptide" in which an immunogen is attached to a molecular needle (hereinafter may be referred to as the composite polypeptide of the present invention);

(2) an "associated product" formed of the composite polypeptide as a monomer (hereinafter may be referred to as the associated product of the present invention);

(3) a "norovirus component vaccine for subcutaneous, intradermal, percutaneous, or intramuscular administration," the vaccine containing the associated product as an active ingredient (protective antigen) (hereinafter may be referred to as the norovirus vaccine of the present invention); and (4) a method for producing the associated product (hereinafter may be referred to as the production method of the present invention).

The "component vaccine" contains an immunization antigen as an essential ingredient. The concept "component vaccine" excludes attenuated live vaccines and toxoids. The immunization antigen employed in the norovirus vaccine of the present invention is the associated product (hexamer) of the present invention serving as a protective antigen.

(1) Composite Polypeptide of the Present Invention

The composite polypeptide of the present invention is a composite polypeptide represented by the amino acid sequence of the following formula (1). In formulas (1) and (2), the symbol "-" connecting the amino acid sequence units denotes a simple molecular bond (substantially a peptide bond), which is used to clearly distinguish the amino acid sequences each having a specific meaning (e.g., W, $L_1$, $X_n$, and Y).

Specifically, the composite polypeptide is represented by $$W\text{-}L_1\text{-}X_n\text{—}Y \quad (1)$$

[wherein W represents an amino acid sequence of a part or the entirety of a virus structural protein as an immunogen; $L_1$ represents a first linker sequence having 0 to 100 amino acids; X represents an amino acid sequence represented by SEQ ID NO: 1; Y represents an amino acid sequence of a cell introduction domain; and repetition number n of X is an integer of 1 to 3], wherein the amino acid sequence of the cell introduction domain Y is represented by the following formula (2):

$$Y_1\text{-}L_2\text{-}Y_2\text{-}Y_3 \quad (2)$$

[wherein $Y_1$ represents any one amino acid sequence selected from the group consisting of SEQ ID NOs: 2 to 5; $Y_2$ represents any one amino acid sequence selected from the group consisting of SEQ ID NOs: 6 to 9; $L_2$ represents a second linker sequence having 0 to 30 amino acids; $Y_3$ represents an amino acid sequence for modification; and either of $Y_2$ and $Y_3$ may be absent].

The number (n) of repetition of amino acid sequence X in $X_n$ is preferably 1, but may be 2 or 3.

In the above formula (1), the amino acid sequence represented by $X_n$, $Y_1$, or $Y_2$ includes a modified amino acid sequence thereof obtained by deleting, substituting, or adding one or more amino acid residues from, with, or to the original amino acid sequence. The term "deleting" refers to deletion of any amino acid residue in the amino acid sequence included in formula (1) and represented by any of the SEQ ID NOs. The amino acid residue at the N-terminal side of the deleted amino acid residue and that at the C-terminal side of the deleted amino acid residue are linked via a peptide bond. In the case of deletion of the N-terminal amino acid residue or the C-terminal amino acid residue, no linkage is present. The number of deleted residues is counted as "the number of amino acid deletions." The term "substituting" refers to substitution of any amino acid residue in the amino acid sequence included in formula (1) and represented by any of the SEQ ID NOs, "with another amino acid residue." The new amino acid residue is linked to the amino acid residue at the N-terminal side thereof and at the C-terminal side thereof via a peptide bond. In the case of substitution of the N-terminal side or C-terminal side amino acid residue, the amino acid residue is linked via a peptide bond to another C-terminal side or N-terminal side amino acid residue. The number of substituted residues is counted as "the number of amino acid substitutions." The term "adding" refers to addition of one or more new amino acid residues to one or more peptide bond sites in the amino acid sequence included in formula (1) and represented by any of the SEQ ID NOs, to thereby form a new peptide bond(s). The type and number of the above modifications of amino acid residue may be elucidated by comparison in alignment of the amino acid sequence represented by formula (1) with the resultant amino acid sequence through manpower or employment of appropriate analysis software.

The linker sequence $L_1$ or $L_2$, or the modification amino acid sequence $Y_3$ may have any desired sequence within the range of the number of amino acid residues as defined in formula (1).

Further, the hexamer (as described below) of the modified composite polypeptide having the modified amino acid sequence preferably has substantially the same immunostimulation activity as that of the hexamer of the composite polypeptide of formula (1). The expression "substantially the same" refers to such a similarity that no significant difference in immunostimulation activity between the hexamer of the composite polypeptide having the original amino acid sequence and the hexamer of the modified composite polypeptide having the modified amino acid sequence is confirmed within a significance level range of 5%, when the immunostimulation activity is determined through an established technique such as the "neutralization test."

In the modified amino acid sequence obtained through deletion, substitution, or addition of one or more amino acid residues from, with, or to the amino acid sequence represented by $X_n$, $Y_1$, or $Y_2$ included in formula (1), the number of modifications of amino acid residues in each amino acid sequence is preferably ≤8n, more preferably ≤4n, still more preferably ≤2n in the case of $X_n$; preferably ≤30, more preferably ≤20, still more preferably ≤10 in the case of $Y_1$; and preferably ≤15, more preferably ≤10, still more preferably ≤5 in the case of $Y_2$.

(2) Associated Product of the Present Invention

The associated product of the present invention is formed of the aforementioned composite polypeptide of the present invention as a monomer. Virtually, the associated product is a trimer (hereinafter may be referred to as the trimer of the present invention) or a hexamer (hereinafter may be referred to as the hexamer of the present invention). The associated product of the present invention, per se, can exert an effect to penetrate cells.

The trimer protein of the present invention is formed of the composite polypeptide of the present invention as a monomer (protein), wherein the polypeptide monomers may be identical to or different from one another. The hexamer of the present invention is a hexamer protein formed through association of two molecules of the trimer protein.

(3) The Norovirus Vaccine of the Present Invention

The norovirus vaccine of the present invention contains the hexamer of the present invention as an active ingredient (protective antigen). The vaccine is a component vaccine against infection with norovirus and administered in a subcutaneous, intradermal, percutaneous, or intramuscular manner. W which is an amino acid sequence of a part or the entirety of the virus structural protein as an immunogen, is an amino acid sequence of a part or the entirety of P domain of the capsid protein of norovirus.

(4) The Production Method of the Present Invention

The production method of the present invention is a method for producing a composite polypeptide associated product. In the production method, 3 or more molecules of the composite polypeptide of the present invention are brought into contact with one another by mediation of an aqueous liquid, to thereby associate the composite polypeptide molecules as monomers to form a trimer and a hexamer, and the trimer or the hexamer is selectively isolated and recovered.

The composite polypeptide of the present invention per se is formed by genetically expressing a nucleic acid fragment encoding the target composite polypeptide. Alternatively, the composite polypeptide is synthesized through a technique of peptide synthesis. When the composite polypeptide molecules are in contact with one another in an aqueous liquid, a trimer and a hexamer of the composite polypeptide are spontaneously formed. As a result, a mixture of a trimer and a hexamer of the composite polypeptide is provided. Through selectively isolating and recovering the trimer or the hexamer, the composite polypeptide of interest of the present invention (trimer or hexamer) can be yielded.

The "aqueous liquid" will next be described. Particularly when the composite polypeptide of the present invention is genetically produced, the composite polypeptide is biologically formed through gene expression. After the production, cells in which the target polypeptide has been formed are collected, and broken or lysed to expose the composite polypeptide, and the target composite polypeptide is isolated through a known isolation method. These steps are performed in an aqueous liquid such as water or a buffer. In the aqueous liquid, association proceeds spontaneously, to thereby yield a mixture of the trimer and the hexamer, which are the associated products of the present invention. Alternatively, when the composite polypeptide of the present invention is produced in whole through chemical synthesis, or produced by synthetizing each divided part and linking them through a chemical modification method, the product is suspended in an aqueous liquid such as water or a buffer. In this case, association spontaneously proceeds, to thereby yield a mixture of the trimer and the hexamer, which are the associated products of the present invention.

No particular limitation is imposed on the method of isolating and recovering the trimer or the hexamer from the mixture, and a known molecular-weight-basis separation method, such as gel electrophoresis, affinity chromatography, molecular sieve separation (e.g., size exclusion chromatography), and ion-exchange chromatography, may be employed.

Thus, one preferred mode of the production method of the present invention is "a method for producing a composite polypeptide associated product, the method comprising culturing a transformant into which a nucleic acid fragment encoding the composite polypeptide of the present invention has been incorporated, in a liquid culture medium, to thereby form the composite polypeptide through gene expression;

obtaining a mixture of a trimer and a hexamer of the composite polypeptide (as a monomer), the mixture being formed via a spontaneous association process; and selectively isolating and recovering the trimer or the hexamer from the mixture."

The thus-produced associated product of the present invention (trimer or hexamer) is purified through a known method, to thereby provide a potentially active ingredient of vaccine. The norovirus vaccine of the present invention is an example of vaccine.

Effects of the Invention

The present invention can provide the following (1) to (3):

(1) a composite polypeptide (monomer) in which a virus structural protein (immunogen) has been attached to a molecular needle, with an expected use as an essential unit of an active ingredient (protective antigen) of a component vaccine for efficiently introducing the virus structural protein (immunogen) into target tissue cells through subcutaneous, intradermal, percutaneous, or intramuscular administration;

(2) an associated product which is a trimer or a hexamer of the composite polypeptide, with an expected use of the active ingredient (protective antigen), and a production method for the associated product; and, as an example of the component vaccines, (3) a norovirus component vaccine containing the hexamer of the composite polypeptide to which P domain of the capsid protein of the norovirus serving as an immunogen has been attached, wherein the component vaccine can induce the target immunoreaction through efficiently introducing the hexamer as a protective antigen into the target tissue cells via subcutaneous, intradermal, percutaneous, or intramuscular administration.

BRIEF DESCRIPTION OF THE SEVERAL VIEWS OF THE DRAWINGS

FIG. 1

A scheme of forming the associated products of the present invention (trimer and hexamer) from the composite polypeptide of the present invention.

FIG. 2

A graph showing results of size exclusion column chromatography of "PN-Saga PF," which is an example of the associated product of the present invention.

FIG. 3

A gel filtration chromatographic chart in separation of the associated product of the present invention (hexamer).

FIG. 4

A graph showing test results of rise (in vivo) in antibody titer by subcutaneous administration of the norovirus vaccine of the present invention, indicating the value of the invention.

DETAILED DESCRIPTION OF THE INVENTION

Modes for Carrying Out the Invention (1) The Composite Polypeptide of the Present Invention The composite polypeptide is represented by the following formula (1):

$$W\text{-}L_1\text{-}X_n\text{—}Y \quad (1)$$

[wherein W represents an amino acid sequence of a part or the entirety of a virus structural protein as an immunogen; $L_1$ represents a first linker sequence having 0 to 100 amino acids; X represents an amino acid sequence represented by SEQ ID NO: 1; Y represents an amino acid sequence of a cell introduction domain; and n of X is an integer of 1 to 3].

Examples of the immunogen W include an amino acid sequence based on a part or the entirety of the peptide structure of the virus structural protein. The wording "based on" refers to the immunogen W including not only the original peptide structure but also a modified amino acid sequence such as a detoxicated amino acid sequence obtained by modifying the original amino acid sequence.

The entirety or a part of the virus structural protein is preferably a part or the entirety of a surface portion including the antigen-presenting part. An example thereof is a part or the entirety of P domain of the capsid protein, which serves as the immunogen of the norovirus vaccine of the present invention.

The first linker sequence $L_1$ is required for appropriately maintaining the distance between the immunogen W and the molecular needle part Y, to thereby suppress steric hindrance. Generally, the number of amino acid residues is preferably larger, as the molecular weight of the immunogen W increases. As described above, the number of amino acid residues is 0 to 100, preferably 10 to 40.

X is an amino acid residue represented by SEQ ID NO: 1, and the amino acid sequence $X_n$ is a sequence of repeating unit Xs with the number of repetitions n (n is an integer). The mode of repetition is linear repetition. The case of $X_2$ means "X-X" (wherein symbol "-" denotes a peptide bond). Also, in the repeated sequence $X_n$, the amino acid sequence may be modified in the aforementioned manner. As mentioned above, the number n is an integer of 1 to 3. The number n is preferably 1 but may be 2 or 3. The repeated sequence $X_n$ (n=2 or 3) is employed for consistently maintaining the suitable distance between the molecular needle Y and the immunogen W in response to the dimension and characteristics of the immunogen W.

The cell introduction domain Y is a basement of the molecular needle and is based on the tail needle of a bacteriophage (i.e., cell-penetrating part). The domain Y is a polypeptide represented by the following formula (2):

$$Y_1\text{-}L_2\text{-}Y_2\text{-}Y_3 \quad (2)$$

[wherein $Y_1$ represents an amino acid sequence selected from the group consisting of SEQ ID NOs: 2 to 5; $Y_2$ represents an amino acid sequence selected from the group consisting of SEQ ID NOs: 6 to 9; $L_2$ represents a second linker sequence having 0 to 30 amino acids; $Y_3$ represents an amino acid sequence for modification of interest; and $Y_2$ or $Y_3$ may be absent].

In $Y_1$ of formula (2), the amino acid sequence from the end of the N-terminal side to the 32 amino acid residue (32 Leu) corresponds to the amino acid sequence of a triple helix β-sheet structure of the bacteriophage T4. The N-terminal amino acid of valine (1 Val) may also be leucine (1 Leu). The remaining C-terminal amino acid sequence is an amino acid sequence of the needle protein of the bacteriophage on the C-terminal side. Examples of the amino acid sequence that can be used at C-terminus of $Y_1$ include an amino acid sequence of gp5 of bacteriophage T4, an amino acid sequence of gpV of bacteriophage P2, an amino acid sequence of gp45 of bacteriophage Mu, and an amino acid sequence of gp138 of bacteriophage ϕ92. More specific examples of $Y_1$ include the amino acid sequence (SEQ ID NO: 2) which has the amino acid sequence of gp5 of bacteriophage T4 on the C-terminal side, the amino acid sequence (SEQ ID NO: 3) which has the amino acid sequence of gpV of bacteriophage P2 on the C-terminal side, the amino acid sequence (SEQ ID NO: 4) which has the amino acid sequence of gp45 of bacteriophage Mu on the C-terminal side, and the amino acid sequence (SEQ ID NO: 5) which has the amino acid sequence of gp138 of bacteriophage ϕ92 on the C-terminal side. The nucleotide sequence encoding the amino acid sequence of $Y_1$ may be selected in accordance with a generally known amino acid-nucleobase relationship.

$Y_2$ in formula (2) is an amino acid sequence of a domain "foldon" of bacteriophage T4 or an amino acid sequence of a domain "tip" of bacteriophage P2, bacteriophage Mu, or bacteriophage ϕ92. The foldon or the tip is a domain forming the tip portion of the molecular needle structure (i.e., fibritin) of bacteriophage. In formula (2), $Y_2$ is not necessarily present. However, when it includes the amino acid sequence of the foldon or the tip, the efficiency of incorporation of the molecular needle to the cell membrane can be enhanced. Thus, the presence of $Y_2$ is preferred. The amino acid sequence of the foldon of bacteriophage T4 is represented by SEQ ID NO: 6. The nucleotide sequence encoding the amino acid sequence may be selected in accordance with a generally known amino acid-nucleobase relationship.

The amino acid sequence of the tip of bacteriophage P2 is represented by SEQ ID NO: 7. The nucleotide sequence encoding the amino acid sequence may be selected in accordance with a generally known amino acid-nucleobase relationship. The amino acid sequence of the tip of bacteriophage Mu is represented by SEQ ID NO: 8. The nucleotide sequence encoding the amino acid sequence may be selected in accordance with a generally known amino acid-nucleobase relationship. The amino acid sequence of the tip of bacteriophage ϕ92 is represented by SEQ ID NO: 9. The nucleotide sequence encoding the amino acid sequence may be selected in accordance with a generally known amino acid-nucleobase relationship.

$L_2$ serves as a second linker intervening between $Y_1$ and $Y_2$. The number of amino acid residues in linker $L_2$ is 0 to 30, preferably 0 to 5. The number of amino acid residues in linker $L_2$ of 0 means the absence of second linker $L_2$.

$Y_3$ is an amino acid sequence for modification and may be selectively incorporated into Y. The modification amino acid sequence is added in order to purify or protect protein (or for another reason), and examples thereof include tag proteins such as histidine tag, GST tag, and FLAG tag. An appropriate linker sequence may be incorporated into $Y_3$. Such an additional linker sequence may also be a component of the amino acid sequence of $Y_3$.

The composite polypeptide of the present invention may be produced through a known method; specifically, a genetic engineering process or chemical synthesis. The entirety of the composite polypeptide of the present invention may be produced in a single process. Alternatively, segments of the polypeptide are individually produced, and the produced segments are linked through a chemical modification method, to produce the composite polypeptide. In one linking procedure of polypeptides by mediation of a linker (e.g., $L_1$ or $L_2$), a lysine residue or a cysteine residue of one polypeptide may be linked to that of another polypeptide by mediation of a linker having a succinimido group or a maleimido group.

In a genetic engineering process, a nucleic acid fragment encoding the entirety of a part of the target composite polypeptide of the present invention may be expressed in host cells (e.g., *Escherichia coli*, yeast, insect cells, and animal cells) or in a cell-free expression system such as an *E. coli* extract, a rabbit reticulocyte extract, or a wheat germ extract. Any nucleic acid expression vector suited for the expression system may be used. Examples of the expression vector include pET (for expression in *E. coli*), pAUR (for expression in yeast), pIEx-1 (for expression in insect cells), pBApo-CMV (for expression in animal cells), and pF3A (for expression in wheat germ extract).

Regarding chemical synthesis, any known method for chemically synthesizing peptides may be employed. More specifically, the entirety or a part of the composite polypeptide of the present invention may be produced through any established customary method (e.g., liquid phase peptide synthesis or solid phase peptide synthesis). Among generally known suitable solid phase peptide synthesis techniques (i.e., chemical synthesis), a Boc solid phase method or an Fmoc solid phase method may be employed. Also, as described above, a ligation technique may be employed in accordance with need. Needless to say, each amino acid may be produced through a known method, and a commercial product thereof may be used.

(2) The Associated Product of the Present Invention

FIG. 1 is a scheme of forming the associated products of the present invention (trimer and hexamer) from the composite polypeptide of the present invention. In FIG. 1, reference numeral 10 denotes the composite polypeptide of the present invention in the form of monomer. Reference numeral 30 denotes the trimer of the present invention, and reference numeral 60 denotes the hexamer of the present invention.

The composite polypeptide 10 of the present invention is formed of a "molecular needle domain 13 corresponding to $X_n$ and Y in formula (1)" in which a "base part 131 corresponding to $X_n$ formula (1) and $Y_1$ in formula (2)" is linked to a "foldon 132 corresponding $Y_2$ in formula (2)," and an "immunogen 11 corresponding to W in formula (1)," wherein two components are linked together via a "linker 12 corresponding to $L_1$ in formula (1). A linker other than linker 12, and the modification sequence corresponding to $Y_3$ in formula (2) are not illustrated. The composite polypeptide 10 of the present invention per se substantially exhibits no function of penetrating the cell membrane of the target tissue cells.

The trimer 30 is a spontaneously associated product of three molecules of the composite polypeptide 10 serving as a monomer via a spontaneous association process. In the trimer 30, 3 units of the molecular needle domain 13 are combined with association via formation of C-terminal-C-terminal bonds, to thereby provide a trimer parallel β-sheet structure, and a helix structure of the β-sheet structure per se (i.e., triple helix β-sheet structure), which corresponds to a needle structure. As a result, a molecular needle 13×3 is formed. The molecular needle 13×3 is composed of a basic part 131×3 and a foldon aggregate 132×3. In this way, a "molecular needle" which has a target tissue cell membrane penetration function is formed through trimerization and a self-assembly process. Three linkers ($\mathbf{12}^1$, $\mathbf{12}^2$, $\mathbf{12}^3$) originating from the respective monomers, and three immunogen portions ($\mathbf{11}^1$, $\mathbf{11}^2$, $\mathbf{11}^3$) linked to the respective linkers exist in the outside area of the molecular needle 13×3.

The hexamer 60 is formed through linking 2 units of the trimer 30, with formation of a bond between the N-terminals of the molecular needle basic parts $(\mathbf{13}\times3)^1$ and $(\mathbf{13}\times3)^2$. The hexamer 60 also exhibits a target tissue cell membrane penetration function. Six linkers ($\mathbf{12}^1$, $\mathbf{12}^2$, $\mathbf{12}^3$, $\mathbf{12}^5$, $\mathbf{12}^6$, $\mathbf{12}^4$ (not illustrated)) originating from the respective trimers, and six immunogen portions ($\mathbf{11}^1$, $\mathbf{11}^2$, $\mathbf{11}^3$, $\mathbf{11}^5$, $\mathbf{11}^6$, $\mathbf{11}^4$ (not illustrated) lined to the respective linkers exist in the outside area of two molecular needles $(\mathbf{13}\times3)^1$ and $(\mathbf{13}\times3)^2$.

Trimerization of the composite polypeptide 10 of the present invention to the trimer 30 and dimerization of the trimer 30 to the hexamer 60 proceed spontaneously in aqueous liquid, and the product exists as the trimer or the hexamer in a stable state. The stability of the trimer or hexamer is remarkably high. For example, the trimer or hexamer is stable in an aqueous liquid at 100° C., in an aqueous liquid at a pH of 2 to 11, or in an aqueous liquid containing 50 to 70 vol. % of organic solvent. In addition, the trimer or hexamer is excellent in safety. When being isolated from the aqueous liquid and dried, the trimer or hexamer is highly stable and retains an excellent cell membrane penetration function.

As described above, transformation of the composite polypeptide of the present invention to the associated product of interest proceeds spontaneously. Generally, most are the hexamers (final form), but some remains as the trimers.

(3) The Norovirus Vaccine of the Present Invention

The associated product of the present invention (hexamer), serving as an active ingredient of the norovirus vaccine of the present invention, exhibits excellent cell penetration function and immunogenicity. Thus, when administered to target tissue cells via subcutaneous administration, intradermal administration, percutaneous administration, or intramuscular administration, the vaccine of the invention efficiently transfers a part or the entirety of P domain of the capsid protein of a norovirus (immunogen) to the target tissue cells, to thereby attain immunization. As a result, the efficacy and safety of the norovirus component vaccine via subcutaneous administration, intradermal administration, percutaneous administration, or intramuscular administration are expected to be enhanced.

The norovirus vaccine of the present invention is provided as a pharmaceutical composition (liquid form) for subcutaneous administration, intradermal administration, percutaneous administration, or intramuscular administration, which contains, as an active ingredient (protective antigen), a "hexamer including, as W, the P domain of the capsid protein of norovirus," among the associated product as described above. In the case where the associated product of the present invention (hexamer) is directly administered, the associated product is subcutaneously, intradermally, percutaneously, or intramuscularly administrated in liquid form which is prepared upon use by suspending and mixing the associated product of the present invention (hexamer) in a buffer or the like. This form is also included in the pharmaceutical composition.

The norovirus vaccine of the present invention may be prepared in a form of a pharmaceutical composition by blending the associated product of the present invention (hexamer) serving as the active ingredient (protective antigen) with an optional adjuvant and an appropriate pharmaceutical carrier. The pharmaceutical carrier may be selected in accordance with the form of use. Examples of the pharmaceutical carrier which may be used in the invention include a filler, an extender, a binder, a humectant, a disintegrant, a surfactant, an excipient, and a diluent. As described above, the form of the composition is generally liquid, but may be a dry product, powder, granule, and the like which are diluted with liquid upon use.

In the norovirus vaccine of the present invention, the amount of the associated product of the present invention (hexamer) is not necessarily fixed and may be appropriately chosen. Generally, it is preferably in a liquid form which contains 1 to 10 mass % of the associated product of the present invention (hexamer) upon administration. The appropriate single dose of administration (inoculation) is about 0.01 μg to about 10 mg for an adult. As needed, initial inoculation may be appropriately combined with booster inoculation. The administration (inoculation) may be carried out one or more times.

EXAMPLES

The present invention will next be described in detail by way of example.

[Example 1] Preparation of the Associated Product of the Present Invention (1) Preparation of the Composite Polypeptide of the Present Invention In Example 1, four composite polypeptides falling within the scope of the present invention and having different immunogens (the following (a), (b), (c), and (d)) were prepared through a genetic engineering technique.

(a) MNV-PF:

a composite polypeptide falling within the scope of the present invention employing, as an immunogen, the entirety of one unit of "P domain Full (PF domain)" prepared by deleting N-terminal domain and Shell domain from "VP-1 domain" of a mouse norovirus (hereinafter may be referred to as "MNV PF"). The amino acid sequence of the immunogen is represented by SEQ ID NO: 10. The nucleotide sequence encoding the amino acid sequence may be selected in accordance with a generally known amino acid-nucleobase relationship.

(b) MNV-P2:

a composite polypeptide falling within the scope of the present invention employing, as an immunogen, only "P2 domain," among capsid-inside "P1 domain" and capsid-outside "P2 domain" which constitute one unit of "PF domain (P domain Full: PF)" prepared by deleting N-terminal domain and Shell domain from "VP-1 domain" of a mouse norovirus. The amino acid sequence of the immunogen is represented by SEQ ID NO: 11. The nucleotide sequence encoding the amino acid sequence may be selected in accordance with a generally known amino acid-nucleobase relationship.

(c) Saga PF:

a composite polypeptide falling within the scope of the present invention employing, as an immunogen, the entirety of one unit of "P domain" (P domain Full: PF)—one viral capsid antigen of human norovirus. The amino acid sequence of the immunogen is represented by SEQ ID NO: 12. The nucleotide sequence encoding the amino acid sequence may be selected in accordance with a generally known amino acid-nucleobase relationship.

(d) Saga P2:

a composite polypeptide falling within the scope of the present invention employing, as an immunogen, only capsid-outside "P2 domain," among capsid-inside "P1 domain" and capsid-outside "P2 domain which constitute one unit of "P domain" (P domain Full: PF)—one viral capsid antigen of human norovirus. The amino acid sequence of the immunogen is represented by SEQ ID NO: 13. The nucleotide sequence encoding the amino acid sequence may be selected in accordance with a generally known amino acid-nucleobase relationship.

<Production of Plasmid for Forming "PN-Saga PF" Via Expression>

"PN-Saga PF" is a composite polypeptide represented by the aforementioned formula (1):

$$W\text{-}L_1\text{-}X_n\text{—}Y \quad (1)$$

wherein Y represents a cell introduction domain represented by formula (2):

$$Y_1\text{-}L_2\text{-}Y_2\text{-}Y_3 \quad (2).$$

In the above formulas, the immunogen W is "Saga PF" represented by amino acid sequence SEQ ID NO: 13; the first linker $L_1$ is amino acid sequence SEQ ID NO: 15; the repeating unit of the repeating sequence $X_n$ is amino acid sequence SEQ ID NO: 1; the number n is 1; the amino acid sequence of the molecular needle base $Y_1$ is amino acid sequence SEQ ID NO: 2; the second linker $L_2$ is "SVE"; the amino acid sequence of the foldon $Y_2$ is amino acid sequence SEQ ID NO: 6; and the amino acid sequence of the modification sequence $Y_3$ is amino acid sequence SEQ ID NO: 16 (VEHHHHHH).

As mentioned below, expression plasmid "plasmid pKN1-1" for forming a composite polypeptide in which the immunogen W in the above formulas (1) and (2) is substituted by GFP (green fluorescent protein: SEQ ID NO: 17) was produced. The composite polypeptide expression plasmid of interest was produced by use of plasmid pKN1-1.

Specifically, a plasmid for forming "PN-Saga PF" was produced through the following procedure.

Firstly, the gene fragment corresponding to 461th to 484th amino acid residues of the wac protein of T4 phage was amplified through PCR from the T4 phage genome, followed by cloning to pUC18, to thereby yield a gene encoding the foldon. Subsequently, the plasmid was cut by restriction enzymes EcoRI and SalI, and the product was inserted into a plasmid pET29b (Novagen) treated by EcoRI and XhoI, to thereby yield plasmid pMTf1-3. Also, the gene fragment corresponding to 474th to 575th amino acid residues of gp5 of the T4 phage was amplified through PCR from the T4 phage genome, followed by cloning to pUC18, to thereby yield a gene encoding gp5. Subsequently, the resultant plasmid was cut by restriction enzymes EcoRI and SalI, and the product was inserted into the aforementioned plasmid pMTf1-3 treated by EcoRI and XhoI, to thereby yield plasmid pKA176. Separately, the GFP expression vector provided by Takahasi of Gunma University was cut by restriction enzymes NdeI and EcoRI, to thereby yield a gene encoding the GFP. The product was inserted into the aforementioned plasmid pKA176 treated by restriction enzymes NdeI and EcoRI, to thereby yield plasmid pKN1-1 (plasmid for GFP-gp5f expression).

On the basis of pKN1-1 serving as the plasmid for GFP-gp5f expression, "plasmid pKN1-SagaPF (or simply referred to as "pKN1-SagaPF") serving as a "PN-Saga PF expression plasmid" was produced by replacing the GFP gene moiety of "plasmid pKN1-1" by Saga PF gene as if cassette exchange was done.

More specifically, a linear plasmid fragment (i.e., receptor plasmid fragment) was produced by removing the GFP gene from plasmid pKN1-1. Specifically, an anti-sense primer (SEQ ID NO: 18) for inverted PCR was synthesized immediately upstream of the GFP gene. Furthermore, a sense primer complimentary to the nucleotide sequence of "MDE-LYKE" (SEQ ID NO: 14) moiety of the linker sequence $L_1$ (SEQ ID NO: 15) added to the C-terminal of the GFP protein (SEQ ID NO: 17), was synthesized. Then, by use of the aforementioned antisense primer and the sense primer, inverted PCR was performed with the plasmid pKN1-1 as a template, whereby a linear plasmid fragment free of GFP was yielded as a PCR amplification product (first PCR amplification product).

Subsequently, the Saga PF moiety was amplified, and the product (Saga PF) was incorporated into the above-amplified linear plasmid fragment by use of an In-Fusion cloning kit, as if a cassette was to be inserted. This was carried out through the following PCR process.

The specific procedure is as follows. Firstly, 35-nucleotide sense primer (SEQ ID NO: 20) was synthesized so that the sequence thereof was a 15-nucleotide sense chain nucleotide sequence on the linear vector 5' side and a 20-nucleotide nucleotide sequence on the Saga PF gene sense chain 5' side. In addition, a 35-nucleotide anti-sense primer (SEQ ID NO: 21) was synthesized so that sequence thereof was "a nucleotide sequence of the Saga PF gene 3'-terminal part (corresponding to 7 amino acid residues on the C-terminal amino acid sequence SEQ ID NO: 10 from which the aforementioned linker sequence (SEQ ID NO: 14) had been deleted) and a nucleotide sequence corresponding to MDELY (SEQ ID NO: 30) of the linker sequence MDE-LYKE (SEQ ID NO: 14)." Subsequently, the Saga PF fragment was amplified by use of the anti-sense primer and the sense primer and pHuNoV-Saga 1F (human norovirus GII.4 Saga-1 full-length clone) as a template, to thereby yield a PCR amplification product (second PCR amplification product). The sequence on the sense primer side (SEQ ID NO: 22) of the PCR product overlapped with the sequence on the anti-sense primer side of the linear vector PCR product, and the sequence on the anti-sense primer side (SEQ ID NO: 23) of the PCR product overlapped with the sequence on the sense primer side of the linear vector PCR product. The primer which is served as a cassette to be inserted is designed so that the sequence of the primer overlaps with the liner vector sequence at both terminals, and, while the overlapping sequences are employed to maintain the orientation, the primer is joined to the vector by means of the In-Fusion cloning kit.

Finally, the first PCR amplification product and the second PCR amplification product were linked through fusion of respective overlapping sequences by means of the In-Fusion cloning kit, whereby pKN1-Saga PF was produced.

The thus-produced "pKN1-Saga PF" (i.e., a "PN-Saga PF" expression plasmid) was incorporated into *E. coli*, to thereby mass-produce "PN-Saga PF" through expression. The product was purified and employed in the following experiments.

<Ultracentrifugal Analysis of "PN-Saga PF">

The thus-prepared "PN-Saga PF" was subjected to ultracentrifugal analysis. In the specific procedure, 1.2-μM "PN-Saga PF" was subjected to dialysis with 0.1M sodium phosphate buffer (pH: 7.0), and the product was ultracentrifuged by means of Optimal XL-I analytical ultracentrifuge (Beckman) at 500,000 rpm and 20° C.

FIG. 2 shows the results of analysis (size exclusion column chromatography) of "PN-Saga PF." As shown in FIG. 2, most of the composite polypeptides "PN-Saga PF" were found to be spontaneously self-associated, and exist in the form of a "PN-Saga PF" trimer and a hexamer formed from 2 molecules of the trimer.

[Example 2] Test of Introduction of "PN-Saga P2" into Cells

The procedure of producing "PN-Saga PF" expression plasmid was repeated, except that the immunogen W was "PN-Saga P2" represented by amino acid sequence SEQ ID NO: 13, to thereby produce a "PN-Saga P2" expression plasmid (pKN1-Saga P2). The formation, purification and ultracentrifugal analysis of "PN-Saga P2" were performed in the same manner as employed in the case of "PN-Saga PF." For replacement of the GFP gene, a sense primer SEQ ID NO: 24 and an anti-sense primer SEQ ID NO: 25 were used for PCR. The thus-obtained PCR product was incorporated into the expression vector PCR product by means of the In-Fusion cloning kit in the same manner as mentioned above.

As a result, most of the composite polypeptides "PN-Saga P2" were also found to be spontaneously self-associated, and exist in the form of a "PN-Saga P2" trimer and a hexamer formed from 2 molecules of the trimer.

Then, the PN-Saga P2 was added to a supernatant of an HeLa cell culture, so as to investigate the possibility for PN-Saga P2 including the Saga P2 domain to be introduced into target cells. P2 was detected through immunofluorescence using an anit-Saga-1 VLP antibody.

As a result, Saga P2 protein introduced into the HeLa cells was detected as a green fluorescent signal at many spots, whereby it was confirmed that PN-Saga P2 functioned as had been expected (not illustrated, but a photograph can be submitted upon request).

[Example 3] Studies on "PN-MNV"

The procedure of producing "PN-Saga PF" expression plasmid was repeated, except that the immunogen W was "MNV PF" represented by amino acid sequence SEQ ID NO: 10 or "MNV P2" represented by amino acid sequence SEQ ID NO: 11, to thereby produce a "PN-MNV PF" expression plasmid (pKN1-MNVPF) and a "PN-MNV P2" expression plasmid (pKN1-MNVP2). The procedures of formation, purification, and ultracentrifugal analysis of "PN-MNV PF" and "PN-MNV P2" were performed in the same manner as employed in the case of "PN-Saga PF." For replacement of the GFP gene by the gene of P domain Full, sense primer SEQ ID NO: 26 and anti-sense primer SEQ ID NO: 27 were used in PCR, and for replacement of the GFP gene by the P2 gene of P domain, sense primer SEQ ID NO: 28 and anti-sense primer SEQ ID NO: 29 were used in PCR.

As a result, similar to the case of "PN-Saga PF," most of each of "PN-MNV PF" and "PN-MNV P2" was found to be spontaneously self-associated, and exist in the form of a trimer thereof and a hexamer formed from 2 molecules of the trimer.

Subsequently, introduction of the above "PN-MNV P2" associated product (the associated product of the present invention, also referred to as "PMNVP2 associated product") into HeLa cells as a target was carried out. The results were observed under a confocal microscope.

Firstly, the PMNVP2 associated product was dyed with a fluorescent dye (ATTO520). Specifically, a 7.5 μM suspension of the PMNVP2 associated product in 0.1 M sodium phosphate buffer (pH: 8.3) and a 300 μM ATTO solution in DMSO were mixed at a volume ratio of 2:1 and at ambient temperature so that the total volume was 450 μL. The dyeing reaction was performed at ambient temperature. After completion of dyeing reaction, the product was washed thrice with 0.1 M sodium phosphate buffer (pH: 7.0) by means of Centricon.

The HeLa cells were preliminarily cultured in $5.0\times10^4$ cells/100 μL (DMEM) at 37° C. under 5% $CO_2$. Then, the preculture medium was changed to a new medium (total volume: 90 μL) prepared by mixing DMEM (phenol red (-)) and 0.1M sodium phosphate buffer (pH: 8.3) at a volume ratio of 2:1. The ATTO520-added PMNVP2 associated product was added to the new culture system so that the total PMNVP2 concentration was 5 μM. For introducing the PMNVP2 associated product into the HeLa cells, culturing was performed for 30 minutes under the same culture conditions as mentioned above.

Incorporation of the PNMVP2 associated product into HeLa cells was observed under the following conditions using a confocal microscope (laser confocal microscope A1 (Nikon)).

(1) Wavelength of Laser Light:

Excitation: 405 nm laser/observation (a 450 nm/50 emission filter) and

Excitation: 488 nm laser/observation (a 525 nm/50 emission filter)

(2) Laser Power

Laser power: 405 nm: 1.4, 488 nm: 0.4

As a result, the fluorescent dye-added PNMVP2 associated product was observed as a large number of small bright spots around cell nuclei as dark portions. Thus, the PNMVP2 associated product was found to be introduced into HeLa cells for a very short incubation time of 30 minutes (not illustrated, but a photograph can be submitted upon request).

[Example 4] Mouse Immunization Test (1) Materials

"PN-MNV PF" associated product (PNVPF associated product)

*E. coli* BL21 (DE3), which had been transformed with the "PN-MNV PF" expression plasmid (pKN1-MNVPF) and used in Example 3, was cultured at 37° C. for 6 hours in an LB medium (200 mL, kanamycin concentration: 30 μg/mL).

Subsequently, an aliquot (30 mL) of the culture liquid was added to a 3 L LB medium (kanamycin concentration: 30 μg/mL), and the mixture was cultured at 37° C. When the turbidity (OD 600) reached 0.8 or higher, an IPTG solution was added so as to adjust the final concentration of 1 mM. The resultant mixture was incubated overnight at 20° C. The incubated product was centrifuged at 4° C. and 8,000 rpm, to thereby collect the bacterial cells. The collected bacterial cells were instantly frozen with liquid nitrogen and stored at −80° C.

One tablet of complete, EDTA-free (Roche) was dissolved in Buffer A (0.1M Tris-HCl (pH: 8), 0.5M NaCl, 1 mM DTT, and 5 mM imidazole), and the above bacterial cells (22.4 g) were suspended in the solution. The bacterial cells were broken by ultrasonication. The set of the above operations was performed on ice. Then, the product was centrifuged at 17,500 rpm and 4° C. for 50 minutes, and the supernatant was filtered by means of a 0.8 μm filter. The thus-purified supernatant was further purified through Ni affinity column [HisTrap TMHP Colum (GE Healthcare)] at 4° C. Elution was performed with Buffer A and Buffer B (0.1M Tris-HCl (pH: 8), 0.5M NaCl, 1 mM DTT, and 500 mM imidazole) under linear gradient conditions (5 to 500 mM imidazole). Samples were monitored at 280 nm, and fractions of interest were recovered.

The combined sample obtained through Ni affinity purification was concentrated to a volume of about 10 mL. The product was filtered by means of a 0.2 μm filter. The filtrate was subjected to gel filtration purification by use of HiLoad 26/60 Superdex 200 column (GE Healthcare). The elution was performed by use of Buffer C (20 mM Tris-HCl, 0.5M NaCl, and 1 mM TCEP). The chart of FIG. 3 shows the results.

The molecular weight of each of the fractions shown in FIG. 3 (each fraction is assigned a fraction number along the horizontal axis) was confirmed through Native SDS PAGE (not illustrated). Among fractions in which a band corresponding to a molecular weight of about 300,000 Da (similar to that of the hexamer of interest) was detected, the 36th fraction, which exhibited the sharpest band, was selected. The fraction was employed as a fraction of the PNVPF associated product (hexamer). The trimer thereof may be readily isolated by subjecting the 38th to 40th fractions exhibiting a molecular weight of about ½ of the above molecular weight to a customary procedure such as purification through ion chromatography.

The P domain (MNVPF) of the capsid protein of the mouse norovirus was prepared on the basis of a known gene sequence through a customary method as a recombinant protein produced from *E. coli* as a host. More specifically, a sense primer having, on the N-terminal side of the PF domain of the mouse norovirus, an overlapping portion (15 nucleotides) with the upstream side of the cloning site of the expression vector pET6×HN, and an anti-sense primer having, on the C-terminal side, an overlapping portion (15 nucleotides) with the downstream side of the cloning site of the expression vector pET6×HN, were synthesized according to the protocol of In-Fusion cloning kit. Then, PCR was performed by use of the primers, and the thus-obtained PCR product was cloned to pET6×HN by means of the In-Fusion cloning kit, to thereby yield pET6×HN-MNVPF. The pET6×HN-MNVPF was introduced into *E. coli* BL21, and MNVPF was expressed through a customary method. The resultant *E. coli* cells were broken, and the entire proteins contained therein were solubilized by use of guanidine. As a result, all the proteins were converted to a linear form. By use of 6 HN tags added to MNVPF contained in the solubilized protein, the product was bound to a column of TALON resin according to the manual thereof. Thereafter, MNVPF was dialyzed with PBS(-), and the solvent was completely changed to PBS(-). After adjustment of the concentration, mice were immunized with the thus-purified MNVPF solution in the following manner.

Besides, a 1-mL syringe with a 26G injection needle (product of TERMO), and mice (Japan SLC, C57BL/6J, 6-week, female) were provided.

(2) Method

The test systems employing the following two protective antigens were established.

(a) administration of MNVPF (3.12 μg/200 μL PBS)

(b) administration of hexamer (13.2 μg/200 μL PBS)

Each protective antigen diluted solution (total amount: 200 μL) was subcutaneously injected to each mouse at 5 sites (40 μL/site) of the back thereof by means of a syringe with a 26G injection needle. Three weeks after the injection, blood was collected through the tail of the mouse (primarily immune serum). Then, the equal volume of the same antigen diluted solution was subcutaneously injected again to each mouse at the back thereof. Two weeks after the injection, blood was collected through the tail of the mouse (secondarily immune serum).

<Preparation of Serum Samples from Collected Blood>

Each of the thus-collected blood samples was centrifuged by means of a desktop centrifuge at 15,000 rpm for 1 minute. The supernatant was transferred to an Eppendorf microtube and centrifuged again at 15,000 rpm for 1 minute. The supernatant was transferred to another Eppendorf microtube and employed as a sample for ELISA. ELISA was carried out under the following conditions.

<Conditions of ELISA>

(a) Material

Virus-like hollow particles (VLP) of mouse norovirus

Mouse serum

Anti-norovirus monoclonal antibody (G3B9λm IgG 2a, positive control)

ELISA plate (F96 MAXI SORP NUNC-IMMUNO PLATE, Thermo SCIENTIFIC)

96-well dilution plate (96-well Round Bottom Non-Treated, CORNING)

Tween 20

BSA

PBS

PBST (0.1% Tween 20-added PBS)

PBSB (1% BSA-added PBS)

PBSTB (1% BSA, 0.1% Tween 20-added PBS)

Goat anti-mouse IgG HRP label (Southern Biotech)

OPD substrate (Sigma, 10 mg tablet of o-phenylenediamine dihydrochloride)

$H_2O_2$

OPD buffer (36 g $Na_2HPO_4.12H_2O$+9.6 g citrate (citric acid)+1 L $D_2W$, pH: 5.0)

2N $H_2SO_4$

Plate reader (BIORAD iMark)

(b) Method

A mouse norovirus VLP was mixed with PBS to thereby prepare a 1-μg/mL liquid thereof, and the virus liquid was added to an ELISA plate at 50 μL/well. The ELISA plate was allowed to stand overnight at 4° C. and then washed 4 times with PBST. PBST remaining on the plate was completely wiped off, and new PBSB was added to the plate at 80 μL/well. The plate was allowed to stand for 2 hours at room temperature. Separately, a mouse serum was 20-fold diluted with PBSB by use of a dilution plate. The thus-diluted serum was stepwise (3-fold) diluted, to thereby provide 8 dilution series in total. After the above standing for 2 hours, PBSB was removed from the ELISA plate, and the diluted serum was added to the ELISA plate at 50 μL/well. The plate was allowed to stand at room temperature for 4 hours, and the diluted serum was removed from the ELISA plate. The plate was washed 4 times with PBST, and PBST remaining on the plate was completely wiped off. Next, an HRP-labeled anti-mouse IgG antibody (5,000-fold diluted with PBSTB) was added to the plate at 50 μL/well, and the plate was allowed to stand for 2 hours at room temperature. Thereafter, the HRP-labeled antibody was removed from the ELISA plate, and the plate was washed 5 times with PBST, followed by completely wiping off remaining PBST. Separately, an OPD substrate (10 mg) was dissolved in an OPD buffer (20 mL), and $H_2O_2$ (10 μL) was added thereto, followed by inversion mixing. The OPD substrate solution was added to the ELISA plate at 50 μL/well, and the plate was allowed to stand at room temperature for color development. Thereafter, color development was stopped by adding 2N $H_2SO_4$ to the plate at 50 μL/well. OD490 was measured by means of a plate reader, and the measurements were compared with a positive control to perform concentration calculation.

(3) Results

FIG. 4 is a graph showing the results of ELISA after the above initial inoculation. In FIG. 4, the vertical axis represents the IgG antibody titer (U/ml). As shown in FIG. 4, the antibody titer was found to significantly rise in one sample among the 4 samples in the case where the PMNVPF associated product (hexamer) had been inoculated. A tendency of rising in antibody titer was also observed in 2 of the remaining 3 samples. In the case of MNVPF (control), no substantial rise was observed in antibody titer.

That is, the associated product of the present invention (hexamer) having MNVPF as an immunogen was found to be very excellent as a protective antigen.

The invention claimed is:

1. A composite polypeptide, which comprises a polypeptide of the following formula (1):

W-L1-Xn-Y (1)

wherein W is an amino acid sequence comprising a part or the entirety of a virus structural protein as an immunogen of a vaccine against the virus; L1 is a first linker sequence having 0 to 100 amino acids; X is an amino acid sequence which comprises the amino acid sequence of SEQ ID NO: 1, or which comprises an amino acid sequence with 8 or less amino acid sequence changes as compared to SEQ ID NO: 1; Y comprises an amino acid sequence of a cell introduction domain; and n is an integer between 1 and 3, wherein the cell introduction domain of Y comprises an amino acid sequence of the following formula (2):

Y1-L2-Y2-Y3 (2)

wherein Y1 is an amino acid sequence which comprises the amino acid sequence of any one of SEQ ID NOs: 2 to 5, or which comprises an amino acid sequence with 30 or less amino acid sequence changes as compared to any one of SEO ID NOs: 2 to 5; Y2 is an amino acid sequence which comprises the amino acid sequence of any one of SEQ ID NOs: 6 to 9, or which comprises an amino acid sequence with 15 or less amino acid sequence changes as compared to any one of SEQ ID NOs: 6 to 9; L2 is a second linker sequence having 0 to 30 amino acids; Y3 is an amino acid sequence for modification; and either of Y2 and Y3 may be absent, and wherein said amino acid changes are selected from the group consisting of additions, deletions, and substitutions.

2. The composite polypeptide according to claim 1, wherein $L_1$ comprises the amino acid sequence of SEQ ID NO: 14.

3. A trimer protein comprising a composite polypeptide of claim 1 as a monomer protein, wherein the monomer proteins of said trimer protein are identical to or different from one another.

4. The trimer protein according to claim 3, which includes a parallel β-sheet structure and a helix structure of the parallel β-sheet structure, said parallel β-sheet structure formed by linking $X_n$s and $Y_1$s, respectively, in three molecules of the composite polypeptide, which molecules are identical to or different from one another.

5. A hexamer protein formed through association of two molecules of a trimer protein of claim 3.

6. A component vaccine for subcutaneous, intradermal, percutaneous, or intramuscular administration, wherein said vaccine comprises the hexamer protein of claim 5 as an active ingredient, and wherein W is an amino acid sequence comprising a part or the entirety of a P domain of a norovirus capsid protein.

7. A method for producing a composite polypeptide associated product, said method comprising:

bringing molecules of a composite polypeptide of claim 1 into contact with one another within an aqueous liquid, to thereby form at least one of a trimer and a hexamer; and selectively isolating and recovering the trimer, the hexamer, or both.

8. The method according to claim 7, wherein the method comprises:

culturing, in a liquid culture medium, a transformant into which a nucleic acid fragment encoding the composite polypeptide has been incorporated, to thereby produce molecules of the composite polypeptide through gene expression, wherein said molecules of the composite polypeptide self-associate to form at least one of a trimer and a hexamer; and selectively isolating and recovering the trimer, the hexamer, or both.

* * * * *

SEQUENCE LISTING

```
<160> NUMBER OF SEQ ID NOS: 30

<210> SEQ ID NO 1
<211> LENGTH: 16
<212> TYPE: PRT
<213> ORGANISM: Artificial Sequence
<220> FEATURE:
<223> OTHER INFORMATION: repeating sequence

<400> SEQUENCE: 1

Leu Glu Gly Ser Asn Thr Ile Phe Val Arg Gly Asp Glu Thr Lys Thr
1               5                   10                  15


<210> SEQ ID NO 2
<211> LENGTH: 86
<212> TYPE: PRT
<213> ORGANISM: Bacteriophage T4

<400> SEQUENCE: 2

Val Glu Gly Asn Gly Thr Ile Leu Val Lys Gly Asn Val Thr Ile Ile
1               5                   10                  15

Val Glu Gly Asn Ala Asp Ile Thr Val Lys Gly Asp Ala Thr Thr Leu
            20                  25                  30

Val Glu Gly Asn Gln Thr Asn Thr Val Asn Gly Asn Leu Ser Trp Lys
        35                  40                  45

Val Ala Gly Thr Val Asp Trp Asp Val Gly Gly Asp Trp Thr Glu Lys
    50                  55                  60

Met Ala Ser Met Ser Ser Ile Ser Ser Gly Gln Tyr Thr Ile Asp Gly
65                  70                  75                  80

Ser Arg Ile Asp Ile Gly
                85


<210> SEQ ID NO 3
<211> LENGTH: 125
<212> TYPE: PRT
<213> ORGANISM: Bacteriophage P2

<400> SEQUENCE: 3

Val Glu Gly Asn Gly Thr Ile Leu Val Lys Gly Asn Val Thr Ile Ile
1               5                   10                  15

Val Glu Gly Asn Ala Asp Ile Thr Val Lys Gly Asp Ala Thr Thr Leu
            20                  25                  30

Asp Ala Leu His Ile Arg Phe Pro Asp Gly Ala Val Ile Glu Tyr Glu
```

```
        35                  40                  45

Pro Glu Thr Ser Ala Leu Thr Val Ser Gly Ile Lys Thr Ala Ser Val
    50                  55                  60

Thr Ala Ser Gly Ser Val Thr Ala Thr Val Pro Val Val Met Val Lys
65                  70                  75                  80

Ala Ser Thr Arg Val Thr Leu Asp Thr Pro Glu Val Val Cys Thr Asn
                85                  90                  95

Arg Leu Ile Thr Gly Thr Leu Glu Val Gln Lys Gly Gly Thr Met Arg
            100                 105                 110

Gly Asn Ile Glu His Thr Gly Gly Glu Leu Ser Ser Asn
        115                 120                 125


<210> SEQ ID NO 4
<211> LENGTH: 107
<212> TYPE: PRT
<213> ORGANISM: Bacteriophage Mu

<400> SEQUENCE: 4

Val Glu Gly Asn Gly Thr Ile Leu Val Lys Gly Asn Val Thr Ile Ile
1               5                   10                  15

Val Glu Gly Asn Ala Asp Ile Thr Val Lys Gly Asp Ala Thr Thr Leu
            20                  25                  30

Gly Asp Ala Gly Ile Tyr His His Glu Gly His Arg Ile Arg Leu Thr
        35                  40                  45

Lys Asp Gly Arg Cys Ile Ile Thr Cys Lys Thr Val Glu Val Tyr Ala
    50                  55                  60

Asp Glu Ser Met Thr Val Asp Thr Pro Arg Thr Thr Phe Thr Gly Asp
65                  70                  75                  80

Val Glu Ile Gln Lys Gly Leu Gly Val Lys Gly Lys Ser Gln Phe Asp
                85                  90                  95

Ser Asn Ile Thr Ala Pro Asp Ala Ile Ile Asn
            100                 105


<210> SEQ ID NO 5
<211> LENGTH: 110
<212> TYPE: PRT
<213> ORGANISM: Bacteriophage phi 92

<400> SEQUENCE: 5

Val Glu Gly Asn Gly Thr Ile Leu Val Lys Gly Asn Val Thr Ile Ile
1               5                   10                  15

Val Glu Gly Asn Ala Asp Ile Thr Val Lys Gly Asp Ala Thr Thr Leu
            20                  25                  30

Glu Lys Val Ile Ile Ser Asn Asn Lys Gln Thr Tyr Ala Ser Phe Asp
        35                  40                  45

Pro Asn Gly Asn Ile Ser Val Tyr Asn Thr Gln Gly Met Lys Ile Asp
    50                  55                  60

Met Thr Pro Asn Ser Ile Val Leu Thr Asp Ala Gly Gly Gly Lys Leu
65                  70                  75                  80

Thr Leu Gln Gly Gly Thr Met Thr Tyr Lys Gly Gly Thr Val Asn Leu
                85                  90                  95

Asn Gly Leu Thr Ile Thr Pro Asp Gly Arg Met Thr Asp Ser
            100                 105                 110


<210> SEQ ID NO 6
<211> LENGTH: 27
<212> TYPE: PRT
```

```
<213> ORGANISM: Bacteriophage T4

<400> SEQUENCE: 6

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25


<210> SEQ ID NO 7
<211> LENGTH: 21
<212> TYPE: PRT
<213> ORGANISM: Bacteriophage P2

<400> SEQUENCE: 7

Gly Lys Val Leu His Thr His Lys His Pro Gly Asp Ser Gly Gly Thr
1               5                   10                  15

Thr Gly Ser Pro Leu
            20


<210> SEQ ID NO 8
<211> LENGTH: 23
<212> TYPE: PRT
<213> ORGANISM: Bacteriophage Mu

<400> SEQUENCE: 8

Gly Lys Ser Thr Asp Lys His Ile His Arg Gly Asp Ser Gly Gly Thr
1               5                   10                  15

Thr Gly Pro Met Gln Leu Glu
            20


<210> SEQ ID NO 9
<211> LENGTH: 30
<212> TYPE: PRT
<213> ORGANISM: Bacteriophage phi 92

<400> SEQUENCE: 9

Gly Gly Ile Gly Leu His Thr His Thr His Pro Val Arg Gly Val Glu
1               5                   10                  15

Thr Gly Gly Ser Thr Val Thr Ser Asp Lys Pro Asn Gly Gly
            20                  25                  30


<210> SEQ ID NO 10
<211> LENGTH: 327
<212> TYPE: PRT
<213> ORGANISM: Mouse norovirus

<400> SEQUENCE: 10

Ile Glu Arg Thr Ile Tyr Arg Met Val Asp Leu Pro Val Leu Gln Pro
1               5                   10                  15

Arg Leu Cys Thr His Ala Arg Trp Pro Ala Pro Ile Tyr Gly Leu Leu
            20                  25                  30

Val Asp Pro Ser Leu Pro Ser Asn Pro Gln Trp Gln Asn Gly Arg Val
        35                  40                  45

His Val Asp Gly Thr Leu Leu Gly Thr Thr Pro Val Ser Gly Ser Trp
    50                  55                  60

Val Ser Cys Phe Ala Ala Glu Ala Ala Tyr Glu Phe Gln Ser Gly Ile
65                  70                  75                  80

Gly Glu Val Ala Thr Phe Thr Leu Ile Glu Gln Asp Gly Ser Ala Tyr
                85                  90                  95

Val Pro Gly Asp Arg Ala Ala Pro Leu Gly Tyr Pro Asp Phe Ser Gly
```

```
            100                 105                 110

Gln Leu Glu Ile Glu Val Gln Thr Glu Thr Thr Lys Lys Gly Glu Lys
        115                 120                 125

Leu Lys Val Thr Thr Phe Glu Met Ile Leu Gly Pro Thr Thr Asn Val
    130                 135                 140

Asp Gln Val Pro Tyr Gln Gly Arg Val Tyr Ala Ser Leu Thr Ala Ala
145                 150                 155                 160

Ala Ser Leu Asp Leu Val Asp Gly Arg Val Arg Ala Val Pro Arg Ser
                165                 170                 175

Val Tyr Gly Phe Gln Asp Val Val Pro Glu Tyr Asn Asp Gly Leu Leu
            180                 185                 190

Val Pro Leu Ala Pro Pro Ile Gly Pro Phe Leu Pro Gly Glu Val Leu
        195                 200                 205

Leu Arg Phe Arg Thr Tyr Met Arg Gln Ile Asp Ser Thr Asp Ala Ala
    210                 215                 220

Ala Glu Ala Ile Asp Cys Ala Leu Pro Gln Glu Phe Val Ser Trp Phe
225                 230                 235                 240

Ala Ser Asn Ala Phe Thr Val Gln Ser Glu Ala Leu Leu Leu Arg Tyr
                245                 250                 255

Arg Asn Thr Leu Thr Gly Gln Leu Leu Phe Glu Cys Lys Leu Tyr Ser
            260                 265                 270

Glu Gly Tyr Ile Ala Leu Ser Tyr Ser Gly Ser Gly Pro Leu Thr Phe
        275                 280                 285

Pro Thr Asp Gly Phe Phe Glu Val Val Ser Trp Val Pro Arg Leu Tyr
    290                 295                 300

Gln Leu Ala Ser Val Gly Ser Leu Ala Thr Gly Arg Thr Leu Lys Gln
305                 310                 315                 320

Met Asp Glu Leu Tyr Lys Glu
                325


<210> SEQ ID NO 11
<211> LENGTH: 131
<212> TYPE: PRT
<213> ORGANISM: Mouse norovirus

<400> SEQUENCE: 11

Val Ser Gly Ser Trp Val Ser Cys Phe Ala Ala Glu Ala Ala Tyr Glu
1               5                   10                  15

Phe Gln Ser Gly Ile Gly Glu Val Ala Thr Phe Thr Leu Ile Glu Gln
            20                  25                  30

Asp Gly Ser Ala Tyr Val Pro Gly Asp Arg Ala Ala Pro Leu Gly Tyr
        35                  40                  45

Pro Asp Phe Ser Gly Gln Leu Glu Ile Glu Val Gln Thr Glu Thr Thr
    50                  55                  60

Lys Lys Gly Glu Lys Leu Lys Val Thr Thr Phe Glu Met Ile Leu Gly
65                  70                  75                  80

Pro Thr Thr Asn Val Asp Gln Val Pro Tyr Gln Gly Arg Val Tyr Ala
                85                  90                  95

Ser Leu Thr Ala Ala Ala Ser Leu Asp Leu Val Asp Gly Arg Val Arg
            100                 105                 110

Ala Val Pro Arg Ser Val Tyr Gly Phe Gln Asp Val Met Asp Glu Leu
        115                 120                 125

Tyr Lys Glu
    130
```

<210> SEQ ID NO 12
<211> LENGTH: 322
<212> TYPE: PRT
<213> ORGANISM: Human norovirus

<400> SEQUENCE: 12

```
Pro Phe Thr Val Pro Ile Leu Thr Val Glu Glu Met Thr Asn Ser Arg
1               5                   10                  15

Phe Pro Ile Pro Leu Glu Lys Leu Phe Thr Gly Pro Ser Gly Ala Phe
            20                  25                  30

Val Val Gln Pro Gln Asn Gly Arg Cys Thr Thr Asp Gly Val Leu Leu
        35                  40                  45

Gly Thr Thr Gln Leu Ser Pro Val Asn Ile Cys Thr Phe Arg Gly Asp
    50                  55                  60

Val Thr His Ile Ala Gly Ser Arg Asn Tyr Thr Met Asn Leu Ala Ser
65                  70                  75                  80

Leu Asn Trp Asn Asn Tyr Asp Pro Thr Glu Glu Ile Pro Ala Pro Leu
                85                  90                  95

Gly Thr Pro Asp Phe Val Gly Lys Ile Gln Gly Leu Leu Thr Gln Thr
            100                 105                 110

Thr Lys Gly Asp Gly Ser Thr Arg Gly His Lys Ala Thr Val Tyr Thr
        115                 120                 125

Gly Ser Ala Pro Phe Thr Pro Lys Leu Gly Ser Val Gln Phe Ser Thr
    130                 135                 140

Asp Thr Glu Asn Asp Phe Glu Thr His Gln Asn Thr Lys Phe Thr Pro
145                 150                 155                 160

Val Gly Val Ile Gln Asp Gly Ser Thr Thr His Arg Asn Glu Pro Gln
                165                 170                 175

Gln Trp Val Leu Pro Ser Tyr Ser Gly Arg Asn Val His Asn Val His
            180                 185                 190

Leu Ala Pro Ala Val Ala Pro Thr Phe Pro Gly Glu Gln Leu Leu Phe
        195                 200                 205

Phe Arg Ser Thr Met Pro Gly Cys Ser Gly Tyr Pro Asn Met Asp Leu
    210                 215                 220

Asp Cys Leu Leu Pro Gln Glu Trp Val Gln His Phe Tyr Gln Glu Ala
225                 230                 235                 240

Ala Pro Ala Gln Ser Asp Val Ala Leu Leu Arg Phe Val Asn Pro Asp
                245                 250                 255

Thr Gly Arg Val Leu Phe Glu Cys Lys Leu His Lys Ser Gly Tyr Val
            260                 265                 270

Thr Val Ala His Thr Gly Gln His Asp Leu Val Ile Pro Pro Asn Gly
        275                 280                 285

Tyr Phe Arg Phe Asp Ser Trp Val Asn Gln Phe Tyr Thr Leu Ala Pro
    290                 295                 300

Met Gly Asn Gly Thr Gly Arg Arg Arg Ala Leu Met Asp Glu Leu Tyr
305                 310                 315                 320

Lys Glu
```

<210> SEQ ID NO 13
<211> LENGTH: 135
<212> TYPE: PRT
<213> ORGANISM: Human norovirus

<400> SEQUENCE: 13

```
Leu Ser Pro Val Asn Ile Cys Thr Phe Arg Gly Asp Val Thr His Ile
```

-continued

```
1               5                   10                  15

Ala Gly Ser Arg Asn Tyr Thr Met Asn Leu Ala Ser Leu Asn Trp Asn
            20                  25                  30

Asn Tyr Asp Pro Thr Glu Glu Ile Pro Ala Pro Leu Gly Thr Pro Asp
        35                  40                  45

Phe Val Gly Lys Ile Gln Gly Leu Leu Thr Gln Thr Thr Lys Gly Asp
    50                  55                  60

Gly Ser Thr Arg Gly His Lys Ala Thr Val Tyr Thr Gly Ser Ala Pro
65                  70                  75                  80

Phe Thr Pro Lys Leu Gly Ser Val Gln Phe Ser Thr Asp Thr Glu Asn
                85                  90                  95

Asp Phe Glu Thr His Gln Asn Thr Lys Phe Thr Pro Val Gly Val Ile
            100                 105                 110

Gln Asp Gly Ser Thr Thr His Arg Asn Glu Pro Gln Gln Trp Val Leu
        115                 120                 125

Met Asp Glu Leu Tyr Lys Glu
    130                 135


<210> SEQ ID NO 14
<211> LENGTH: 7
<212> TYPE: PRT
<213> ORGANISM: Artificial Sequence
<220> FEATURE:
<223> OTHER INFORMATION: a part of linker sequence in GFP

<400> SEQUENCE: 14

Met Asp Glu Leu Tyr Lys Glu
1               5


<210> SEQ ID NO 15
<211> LENGTH: 16
<212> TYPE: PRT
<213> ORGANISM: Artificial Sequence
<220> FEATURE:
<223> OTHER INFORMATION: linker sequence in GFP

<400> SEQUENCE: 15

Met Asp Glu Leu Tyr Lys Gln Ser Asn Ser Ser Ser Val Pro Gly Gly
1               5                   10                  15


<210> SEQ ID NO 16
<211> LENGTH: 8
<212> TYPE: PRT
<213> ORGANISM: Artificial Sequence
<220> FEATURE:
<223> OTHER INFORMATION: modification sequence

<400> SEQUENCE: 16

Val Glu His His His His His His
1               5


<210> SEQ ID NO 17
<211> LENGTH: 232
<212> TYPE: PRT
<213> ORGANISM: Artificial Sequence
<220> FEATURE:
<223> OTHER INFORMATION: GFP (green fluorescent protein)

<400> SEQUENCE: 17

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
```

-continued

```
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly
225                 230


<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18

ctgcagatgg atgaactgta                                                   20


<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19

catatgtata tctccttctt                                                   20


<210> SEQ ID NO 20
<211> LENGTH: 35
<212> TYPE: DNA
<213> ORGANISM: Artificial Sequence
<220> FEATURE:
<223> OTHER INFORMATION: primer

<400> SEQUENCE: 20

ttcatccatc tgcagtaaag cacgtctgcg ccccg                                  35


<210> SEQ ID NO 21
```

-continued

<211> LENGTH: 35
<212> TYPE: DNA
<213> ORGANISM: Artificial Sequence
<220> FEATURE:
<223> OTHER INFORMATION: primer

<400> SEQUENCE: 21
ggagatatac atatgccatt tactgtccca atctt 35

<210> SEQ ID NO 22
<211> LENGTH: 15
<212> TYPE: DNA
<213> ORGANISM: Artificial Sequence
<220> FEATURE:
<223> OTHER INFORMATION: primer

<400> SEQUENCE: 22
ttcatccatc tgcag 15

<210> SEQ ID NO 23
<211> LENGTH: 15
<212> TYPE: DNA
<213> ORGANISM: Artificial Sequence
<220> FEATURE:
<223> OTHER INFORMATION: primer

<400> SEQUENCE: 23
ggagatatac atatg 15

<210> SEQ ID NO 24
<211> LENGTH: 35
<212> TYPE: DNA
<213> ORGANISM: Artificial Sequence
<220> FEATURE:
<223> OTHER INFORMATION: primer

<400> SEQUENCE: 24
ttcatccatc tgcaggagca cccattgttg gggtt 35

<210> SEQ ID NO 25
<211> LENGTH: 35
<212> TYPE: DNA
<213> ORGANISM: Artificial Sequence
<220> FEATURE:
<223> OTHER INFORMATION: primer

<400> SEQUENCE: 25
ggagatatac atatgctgtc tcctgtcaac atctg 35

<210> SEQ ID NO 26
<211> LENGTH: 35
<212> TYPE: DNA
<213> ORGANISM: Artificial Sequence
<220> FEATURE:
<223> OTHER INFORMATION: primer

<400> SEQUENCE: 26
ttcatccatc tgcagttgct tgagtgttcg gcctg 35

<210> SEQ ID NO 27
<211> LENGTH: 35
<212> TYPE: DNA
<213> ORGANISM: Artificial Sequence
<220> FEATURE:
<223> OTHER INFORMATION: primer

<400> SEQUENCE: 27

-continued

```
ggagatatac atatgattga gaggactatc tatcg                            35


<210> SEQ ID NO 28
<211> LENGTH: 36
<212> TYPE: DNA
<213> ORGANISM: Artificial Sequence
<220> FEATURE:
<223> OTHER INFORMATION: primer

<400> SEQUENCE: 28

ttcatccatc tgcagcacat cctgaaaacc ataaac                           36


<210> SEQ ID NO 29
<211> LENGTH: 35
<212> TYPE: DNA
<213> ORGANISM: Artificial Sequence
<220> FEATURE:
<223> OTHER INFORMATION: primer

<400> SEQUENCE: 29

ggagatatac atatggtctc tgggtcctgg gtttc                            35


<210> SEQ ID NO 30
<211> LENGTH: 5
<212> TYPE: PRT
<213> ORGANISM: Artificial Sequence
<220> FEATURE:
<223> OTHER INFORMATION: a part of linker sequence in GFP

<400> SEQUENCE: 30

Met Asp Glu Leu Tyr
1               5
```